United States Patent [19]
Fischer et al.

[11] Patent Number: 6,048,997
[45] Date of Patent: Apr. 11, 2000

[54] MANUFACTURING PROCESS FOR 6-AMINOCAPRONITRILE

[75] Inventors: Rolf Fischer, Heidelberg; Rocco Paciello, Bad Dürkheim; Michael Röper, Wachenheim; Werner Schnurr, Herxheim, all of Germany

[73] Assignee: BASF Aktiengesellschaft, Ludwigshafen, Germany

[21] Appl. No.: 09/230,742

[22] PCT Filed: Jul. 23, 1997

[86] PCT No.: PCT/EP97/03988

§ 371 Date: Feb. 1, 1999

§ 102(e) Date: Feb. 1, 1999

[87] PCT Pub. No.: WO98/05632

PCT Pub. Date: Feb. 12, 1998

[30] Foreign Application Priority Data

Aug. 3, 1996 [DE] Germany .......................... 196 31 521

[51] Int. Cl.$^7$ .................................................. C07C 255/00
[52] U.S. Cl. ............................................................ 558/452
[58] Field of Search .............................................. 558/452

[56] References Cited

U.S. PATENT DOCUMENTS

| | | |
|---|---|---|
| 1,477,219 | 12/1923 | Halvorsen . |
| 2,777,873 | 1/1957 | Hasek . |
| 3,461,167 | 8/1969 | Buehler et al. . |
| 3,471,563 | 10/1969 | Brake . |
| 4,769,498 | 9/1988 | Billig et al. . |
| 5,068,398 | 11/1991 | Merger et al. . |

FOREIGN PATENT DOCUMENTS

| | | |
|---|---|---|
| 11 401 | 5/1980 | European Pat. Off. . |
| 96 986 | 12/1983 | European Pat. Off. . |
| 96 988 | 12/1983 | European Pat. Off. . |
| 149 894 | 7/1985 | European Pat. Off. . |
| 214 622 | 3/1987 | European Pat. Off. . |
| 285 420 | 10/1988 | European Pat. Off. . |
| 376 121 | 7/1990 | European Pat. Off. . |
| 472 071 | 2/1992 | European Pat. Off. . |
| 25 19 817 | 11/1976 | Germany . |
| 1 551 741 | 8/1979 | United Kingdom . |
| 93/16034 | 8/1993 | WIPO . |
| 94/26688 | 11/1994 | WIPO . |

OTHER PUBLICATIONS

K. Weissermel, H.J. Arpe, Ind. Org. Chem. 1994, S.268.
Tolman et al., Adv. in Catal., vol. 33, 1985, S.23.

*Primary Examiner*—Johann Richter
*Assistant Examiner*—Joseph Murray
*Attorney, Agent, or Firm*—Keil & Weinkauf

[57] ABSTRACT

Manufacture of 6-aminocapronitrile or 6-aminocapronitrile/hexamethylene diamine mixtures, involving a) the reaction of at least one pentennitrile, selected from the group consisting of 2,3 and 4-pentennitrile with carbon monoxide and hydrogen in the presence of catalysts, which contain at least one element of the eighth subgroup as active components, obtaining a hydrogenation formylating discharge (I), b) the optional separation of carbon monoxide, hydrogen and the catalyst from the hydrogenation formylating discharge (I), obtaining a hydrogenation formylating discharge (II), c) the separation of 5-formyl valeronitrile from the hydrogenation formylating discharge (I) or (II), d) the reaction of separated 5-formyl valeronitrile with ammonia and hydrogen in the presence of hydrogenating catalysts, selected from the group consisting of rhenium, copper and its compounds as well as metals and metallic compounds of the eighth group, obtaining a hydrogenation discharge, and e) obtaining 6-aminocapronitrile and if necessary hexamethylene diamine.

7 Claims, No Drawings

MANUFACTURING PROCESS FOR 6-AMINOCAPRONITRILE

This application is a 371 of PCT/EP97/03998 filed Jul. 23, 1997.

The present invention relates to a process for preparing 6-aminocapronitrile or 6-aminocapronitrile-hexamethylenediamine mixtures.

EP-A 11401 describes the reaction of 3-pentenenitrile with carbon monoxide and hydrogen under superatmospheric pressure in the presence of a cobalt catalyst to obtain a mixture of isomeric formylvaleronitriles and the corresponding alcohols obtained from the aldehydes. The cited reference further describes the reductive amination of δ-cyanovaleraldehyde to hexamethylenediamine. According to Example 4 of the cited reference, a 60% δ-cyanovaleraldehyde mixture was reacted with ammonia and hydrogen at 100° C. and a hydrogen pressure of 140 bar in the presence of Raney nickel for two hours, but the conversion (based on the δcompound) was only 25%. The low conversion shows that the reductive amination of an aldehyde group and the hydrogenation of a nitrile group in one and the same molecule, to a diamine, constitutes a difficult hydrogenation problem. Furthermore, the formation of 6-aminocapronitrile is not described. Moreover, the stream factor of the catalyst used is unsatisfactory for industrial utilization.

U.S. Pat. No. 2,777,873 discloses reductively aminating 5-formylvaleric esters with ammonia and hydrogen in the presence of nickel, cobalt, iron, platinum or palladium catalysts at from 100 to 160° C. and pressures from 1 bis 1000 atmospheres to obtain 6-aminocaproic esters. EP-A 376 121 also describes this reaction for ruthenium catalysts, at temperatures within the range from 80 to 140° C. and pressures within the range from 40 to 1000 bar.

According to U.S. Pat. No. 3,461,167 (column 3, lines 66 to 74), cobalt, copper and rhenium catalysts are suitable for hydrogenation of adiponitrile to hexamethylenediamine in the presence of ammonia. The preferred conditions are 70–170° C. and 300–7000 psi. According to U.S. Pat. No. 3,471,563, this reaction can also be carried out with ruthenium catalysts.

EP-A 214 622 mentions the hydroformylation of 3-butenenitrile in the presence of rhodium/chelate phosphite catalysts in the description.

WO 94/26688 describes a process comprising
(a) isomerizing internal substituted olefins to terminal olefins,
(b) preferentially hydroformylating the terminal olefins in the presence of the internal olefins,
(c) removing the hydroformulation products, and
(d) recycling the internal olefins into the isomerization.

Claim 3 of WO 94/26688 is directed to nitrilic olefins. The hydroformylation catalysts used are rhodium-triphenylphosphine systems in which the triphenylphosphine is rendered soluble in water by suitable functional groups.

WO 95/18783 describes the hydroformylation of internal nitrilic olefins with water-soluble platinum catalysts.

It is an object of the present invention to make available a process for preparing either 6-aminocapronitrile or a mixture of 6-aminocapronitrile and hexamethylenediamine with a very high conversion starting from 2- and/or 3- and/or 4-pentenenitrile. More particularly, the process shall ensure long catalyst on-stream times.

We have found that this object is achieved by a process for preparing 6-aminocapronitrile or 6-aminocapronitrile/hexamethylenediamine mixture, which comprises a) reacting at least one pentenenitrile selected from the group consisting of 2-pentenenitrile, 3-pentenenitrile and 4-pentenenitrile with carbon monoxide and hydrogen in the presence of a catalyst containing at least one element of subgroup eight as active component to obtain a hydroformylation effluent I, b) optionally removing carbon monoxide, hydrogen and the catalyst from the hydroformylation effluent I to obtain a hydroformylation effluent II, c) removing 5-formylvaleronitrile from said hydroformylation effluent I or II, d) reacting the removed 5-formylvaleronitrile with ammonia and hydrogen in the presence of a hydrogenation catalyst selected from the group consisting of rhenium, copper and compounds thereof, and also metals and metal compounds of subgroup eight to obtain a hydrogenation effluent, and e) isolating 6-aminocapronitrile with or without hexamethylenediamine from the hydrogenation effluent.

According to this invention, at least one pentenenitrile selected from the group consisting of 2-pentenenitrile, 3-pentenenitrile or 4-pentenenitrile is used, preferably 3- or 4-pentenenitrile.

3-Pentenenitrile, the most important starting material for the process, can be prepared for example by addition of hydrocyanic acid to butadiene in the presence of nickel(0)/phosphite complexes as catalysts (K. Weissermel, H.-J. Arpe, Industrielle organische Chemie, 4th edition, VCH Verlag Weinheim, 1994, page 268).

2-pentenenitrile and 4-pentenenitrile are obtainable for example by isomerization of 3-pentenenitrile (for example in the presence of nickel(0)/phosphate complexes and Lewis acids, see Tolman et al. in Adv. in Catal., 33 (1985), 23; or in the presence of hydroformylation catalysts under reaction conditions).

The reaction ("hydroformylation") of the pentenenitrile or pentenenitrile mixture is effected according to this invention with carbon monoxide and hydrogen in the presence of a catalyst containing at least one element of subgroup eight as active component to obtain a hydroformylation effluent I.

The hydroformylation is customarily carried out at temperatures within the range from 30 to 180° C., especially from 50 to 130° C., and pressures within the range from 0.01 bar to 100 bar, in particular from 5 bar to 20 bar. The molar ratio used for the mixture of carbon monoxide and hydrogen is generally within the range from 1:100 to 10:1, in particular from 1:20 to 1:2.

In a preferred embodiment, the hydroformylation is carried out in the presence of reaction-inert solvents such as aromatic or cycloaliphatic compounds such as toluene or cyclohexane. Also suitable are high boiling esters such as bis(2-ethylhexyl) phthalate or TEXANOL® (a 2,2,4-trimethylpentane-1,3-diol monoisobutyrate from EASTMAN). Particular preference is given here to those formylvaleronitriles which are produced in the hydroformylation of the pentenenitriles used and also to those higher boiling (relative to the formylvaleronitriles formed) compounds formed during the hydroformylation by condensation of the formylvaleronitriles just described.

The catalysts used according to this invention contain at least one element of subgroup eight such as iron, cobalt, nickel, ruthenium, rhodium, palladium, osmium, iridium or platinum as active components. Particularly preferred elements are cobalt, rhodium and platinum.

In a particularly preferred embodiment, cocatalysts such as lipophilic and hydrophilic ligands are added, especially the sulfonic acid, ammonium or carboxylic acid salts of phosphines, diphosphines, phosphites or di- and also polyphosphites.

At the present date, particularly preferred hydroformylation catalysts are rhodium carbonyl complexes such as rhodium bis(carbonyl)acetylacetonate (Rh(CO)$_2$acac) in conjunction with cocatalysts selected from the group consisting of triarylphosphines such as triphenylphosphine, bis(diarylphosphino)alkanes such as 2,2'-bis-diphenylphosphinomethylbiphenyl or diphenylphosphinoethane, triaryl phosphites such as triphenyl phosphite or tris-2-tert-butylphenyl phosphite and polyphosphites of the formulae I and II, which are known for example from EP-A 472 071, U.S. Pat. No. 4,769,498, EP-A 149 894, EP-A 96 988 and EP-A 96 986.

Polyphosphites of the formula I are

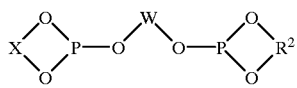   I where

X is a bivalent bisarylene radical or R$^1$,

W is a bivalent substituted or unsubstituted arylene, bisarylene or alkylene radical, and R$^1$ and R$^2$ are identical or different and are each a substituted or unsubstituted alkylene or ortho-arylene radical.

Of the compounds of the formula I, preference is given to those in which the radicals X and W in the formula I are each a bisarylene radical, in particular the radical of the formula IV

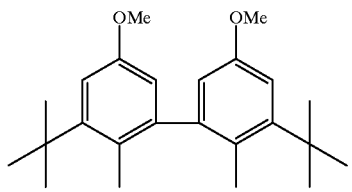   IV and R$^2$ is an ortho-phenylene, 2,2-dimethyl-1,3-propylene or 1,1,2,2-tetramethylethylene radical. Preference is further given to those compounds of the formula I in which W, R$^1$ and R$^2$ are each independently of the others ortho-phenylene, 2,2-dimethyl-1,3-propylene or 1,1,2,2-tetramethylethylene.

The polyphosphites of the formula I can be prepared in a conventional manner by means of a suitably chosen sequence of phosphorus halide/alcohol condensation reaction, for example by a) reacting phosphorus trichloride with a diol to form a monochlorophosphite;

b) reacting this intermediate with a further diol to form the corresponding hydroxyl-substituted diorganophosphite intermediate;

c) reacting this diorganophosphite intermediate with phosphorus trichloride to form the corresponding phosphorus dichloride intermediate;

d) and finally reacting this dichloride with an appropriate diol to form the desired bisphosphite.

While this synthetic route is necessary for preparing asymmetrically substituted phosphites, symmetrically substituted compounds can be prepared by reacting the product of step a) with an appropriate diol in a molar ratio of 2:1.

The condensation reactions mentioned are generally carried out in a suitable solvent, for example toluene, in the presence of an auxiliary base, such as triethylamine, as HCl acceptor.

Examples of suitable compounds of the formula I are:

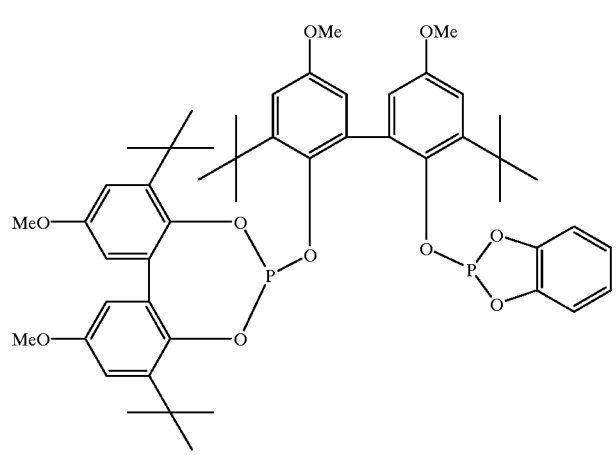   1

-continued
2
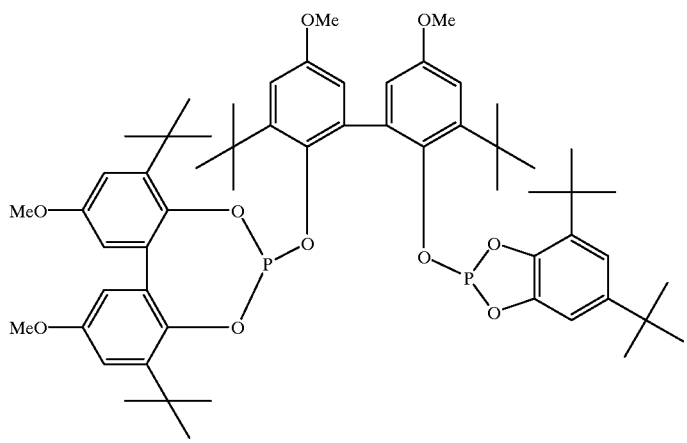
3
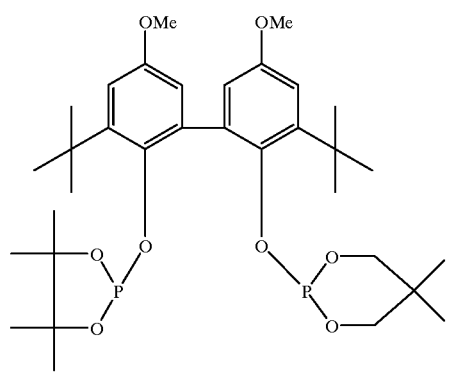
4
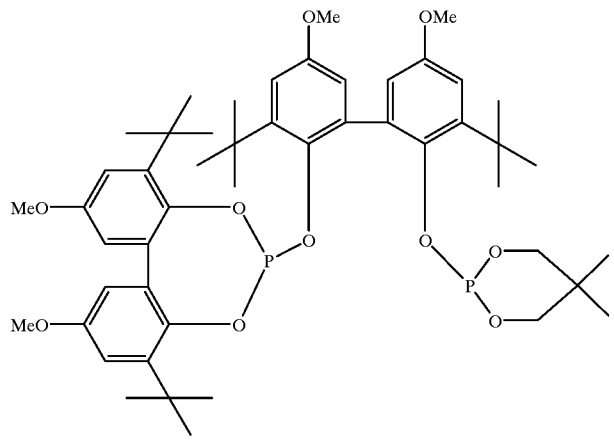
5
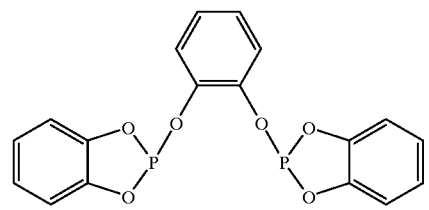

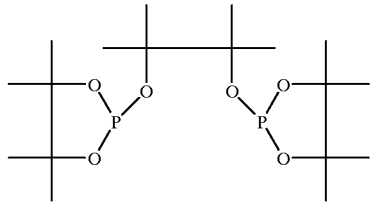

Polyphosphites of the formula II are

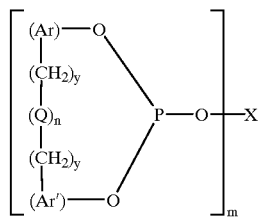

where
Ar and Ar' are identical or different, substituted or unsubstituted arylene radicals having from 6 to 18 carbon atoms;
X is an m-binding radical having from 2 to 30 carbon atoms and selected from the group consisting of alkylene, alkylene-oxy-alkylene, arylene and a radical of the formula arylene-$(CH_2)_y$—$(Q)_n$—$(CH_2)_y$-arylene where the arylene radicals are each as defined above and
y is 0 or 1;
Q is a bivalent bridging group selected from the group consisting of oxygen, sulfur, —CO—, —$CR^3R^4$—, where $R^3$ and $R^4$ are each hydrogen, alkyl having from 1 to 12 carbon atoms or a phenyl, tolyl or anisyl radical, and —$NR^5$—, where $R^5$ is hydrogen or methyl;

n is 0 or 1, and
m is 2, 3, 4, 5 or 6.

In preferred compounds of the formula II, Ar and Ar' are each phenylene, y and n are each 0 and m is 2, in which case the two phenylene radicals are linked to each other in the o-position and can be substituted by alkyl groups having from 1 to 4 carbon atoms or $C_1$–$C_4$-alkoxy groups, especially methoxy and t-butyl groups, in the o- and p-position relative to the bond to the oxygen bridge to the phosphorus atom.

Particular preference is given to the phosphite of the formula III

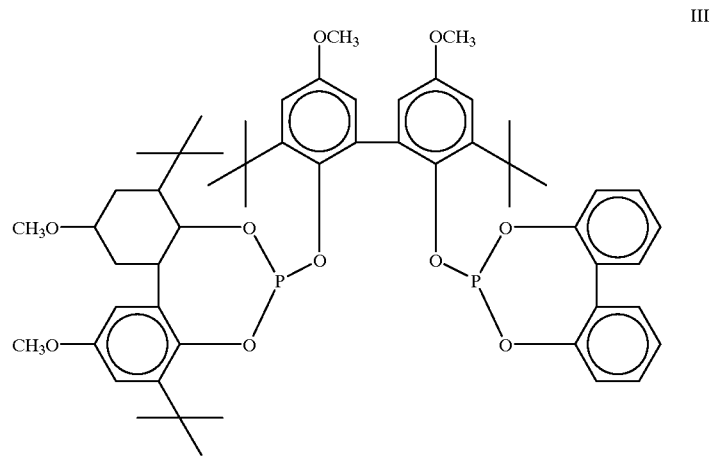

The molar ratio of pentenenitrile to catalyst is generally within the range from 100:1 to 100,000:1, preferably within the range from 500:1 to 10,000:1.

The molar ratio of catalyst to cocatalyst of pentenenitrile is customarily within the range from 1:1:100 to 1:200:100,000, especially within the range from 1:2:500 to 1:100:10,000.

Hydrogen, carbon monoxide, catalyst and any solvent from the hydroformylation are optionally removed from the hydroformylation effluent to obtain a hydroformylation effluent II.

In a particularly preferred embodiment, removed substances—hydrogen, carbon monoxide, catalyst and hydroformylation solvent (if used)—are recycled into the hydroformylation step a).

According to the invention, 5-formylvaleronitrile is removed from the hydroformylation effluent I or II. The removal is preferably effected by distillation.

In a particularly preferred embodiment, high boilers and the catalyst are first removed from the hydroformylation effluents I or II. This is particularly preferably effected using thermally gentle processes as embodied for example in flash evaporators, falling-film evaporators or wiping-blade evaporators in a conventional manner. The removed high boilers and the catalyst, especially rhenium-containing catalysts, can be recycled into the hydroformylation step (step a), if desired.

If cobalt-containing catalysts are used, a preferred embodiment comprises oxidizing the hydroformylation effluents I or II with oxygen, preferably with air, to convert cobalt into a nonvolatile form, especially cobalt(II) salts.

The mixture as freed from high boilers, for example aldol condensation products, and catalyst is preferably subjected to a further distillation to remove low boilers (compared with formylvaleronitriles) such as unconverted pentenenitriles. The pentenenitriles thus recovered can be partly or wholly recycled into the hydroformylation step.

To obtain the desired product of value, 5-formylvaleronitrile, the reaction mixture obtained on removal of pentenenitriles, which predominantly comprises 5-, 4- and 3-formylvaleronitrile, is preferably subjected to a fractional distillation in which 5-formylvaleronitrile (bp 95° C./3 mbar) is separated from a mixture of 4- and 3-formylvaleronitrile (bp 77–81° C./3 mbar). The mixture of the branched formylvaleronitriles is generally removed from the system.

It is surprising that the boiling point difference between 5-formylvaleronitrile and the branched isomers 4- and 3-formylvaleronitrile is sufficient even at low vacuums. For instance, at a pressure of 3 mbar the boiling point difference is 14° C. This means that economically acceptable separation is possible even in the industrially relevant vacuum range, i.e. at pressures not less than 10 mbar.

5-Formylvaleronitrile can of course also be isolated in a different manner, for example by conducting the distillation in only one stage or in two stages.

At the present date, a certain amount of 6-hydroxyvaleronitrile is also formed, depending on the reaction conditions. 6-Hydroxyvaleronitrile is also a product of value in that it can be converted into 6-aminocapronitrile together with or separately from 5-formylvaleronitrile.

If formylvaleronitriles are to be used as solvents, the desired proportion of formylvaleronitrile product is advantageously removed from the system and the remainder recycled.

According to the invention, 5-formylvaleronitrile is reacted with ammonia and hydrogen in the presence of a hydrogenation catalyst in a first step (step a)) at temperatures within the range from 40° C. to 150° C., advantageously within the range from 50° C. to 140° C., in particular within the range from 60° C. to 130° C., and pressures within the range from 2 to 350, advantageously from 20 to 300, bar, in particular in the range from 40 to 250 bar, to obtain a hydrogenation effluent.

The reaction is preferably carried out in liquid ammonia as solvent, in which case the ammonia also serves as reactant. The ammonia quantity is generally from 1 to 80 mol, in particular from 10 to 50 mol, of ammonia per mole of 5-formylvaleronitrile. It can also be advantageous to use, in addition to ammonia, a reaction-inert solvent, for example alcohols, esters, ethers, hydrocarbons, in which case the solvent is generally used in a weight ratio of solvent to 5-formylvaleronitrile within the range from 0.1:1 to 5:1, preferably within the range from 0.5:1 to 3:1. Alcohols such as methanol and ethanol are particularly preferred.

The amount of hydrogen is customarily chosen so that the molar ratio of hydrogen to 5-formylvaleronitrile is within the range from 1:1 to 100:1, in particular within the range from 5:1 to 50:1.

The catalysts used according to the invention are hydrogenation catalysts selected from the group consisting of metals or metal compounds of rhenium, copper and the elements of subgroup eight (hereinafter called "hydrogenation metals"), especially iron, cobalt, nickel, ruthenium, rhodium, palladium, osmium, iridium and platinum, particularly preferably ruthenium, cobalt, palladium and nickel, with the proviso that the hydrogenation catalyst does not contain copper, nickel or copper and nickel as sole components.

The catalysts which are usable according to the invention can be supported or unsupported catalysts. Suitable support materials include for example porous oxides such as aluminum oxide, silicon dioxide, alumosilicates, lanthanum oxide, titanium dioxide, zirconium dioxide, magnesium oxide, zinc oxide and zeolites and also activated carbon or mixtures thereof.

The catalysts can be used as fixed-bed catalysts in upflow or downflow operation or as suspension catalysts. The space velocity over the catalyst is preferably chosen within the range from 0.1 to 2.0, preferably 0.3 to 1, kg of 5-formylvaleronitrile/l of catalyst • hour.

It is also possible to use compounds of the abovementioned metals as homogeneously dissolved hydrogenation catalysts.

In a preferred embodiment, the abovementioned catalysts may further contain from 0.01 to 25, preferably from 0.1 to 5, % by weight, based on the total amount of hydrogenation metals (calculated as elements), of at least promoter based on a metal selected from the group consisting of copper, silver, gold, manganese, zinc, cadmium, lead, tin, scandium, yttrium, lanthanum and the lanthanide elements, titanium, zirconium, hafnium, chromium, molybdenum, tungsten, vandadium, tantalum, antimony, bismuth, aluminum, and also be doped with from 0.01 to 5, preferably from 0.1 to 3, % by weight, based on the hydrogenation metals (calculated as elements), of a compound based on an alkali metal or an alkaline earth metal, preferably alkali metal and alkaline earth metal hydroxides such as lithium hydroxide, sodium hydroxide, potassium hydroxide, rubidium hydroxide, cesium hydroxide, particularly preferably lithium hydroxide.

The catalysts used in the process of this invention can be, for example, precipitation catalysts. Such catalysts can be prepared by precipitating their catalytically active components from their salt solutions, especially from the solutions of their nitrates and/or acetates, for example by additions of solutions of alkali metal and/or alkaline earth metal hydroxide and/or carbonate solutions, for example sparingly soluble hydroxides, oxide hydrates, basic salts or carbonates, then drying the resulting precipitates and subsequently converting them by calcination at temperatures within the range from generally 300 to 700° C., in particular from 400 to 600° C., into the corresponding oxides, mixed oxides and/or mixed-valent oxides, which, generally by treatment with hydrogen or with hydrogen-comprising gases at cutomarily 50–700° C., in particular 100–400° C., are reduced to the respective metals and/or oxidic compounds of lower oxidation state and so converted into the actual catalytically active form. Here, the reduction is generally carried on to the point where no further water is formed.

In the preparation of precipitation catalysts containing a support material, the precipitation of the catalytically active components can take place in the presence of the support material in question. The catalytically active components, however, can also be advantageously precipitated from the respective salt solutions at the same time as the support material. The process of this invention is preferably carried out using hydrogenation catalysts containing the hydrogenation-catalyzing metals or metal compounds deposited on a support material. As well as the abovementioned precipitation catalysts which, as well as the catalytically active components, additionally contain a support material, suitable support materials for the process of this invention are generally those catalyst materials in which the hydrogenation-catalyzing components have been applied to a support material by impregnation, for example.

The manner in which the catalytically active metals are applied to the support is generally not critical and can be accomplished in various ways. The catalytically active metals can for example be applied to these support materials by saturation with solutions or suspensions of the salts or oxides of the respective elements, drying and subsequent reduction of the metal compounds to the respective metals or compounds of low oxidation state by means of a reducing agent, preferably with hydrogen or complex hydrides.

Another way of applying the catalytically active metals to these supports comprises impregnating these supports with solutions of thermally readily decomposable salts, for example with nitrates, or thermally readily decomposable complexes, for example carbonyl or hydrido complexes, of the catalytically active metals and heating the resulting impregnated support to temperatures within the range from generally 300 to 600° C. to effect thermal decomposition of the adsorbed metal compounds. This thermal decomposition is preferably carried out under a protective gas atmosphere. Suitable protective gases can be, for example, nitrogen, carbon dioxide, hydrogen or a noble gas.

The catalytically active metals can further be applied to the catalyst support by vapor deposition or by flame spraying. The catalytically active metal content of these supported catalysts is not critical in principle for the success of the process of this invention. A person skilled in the art will appreciate that higher catalytically active metal contents of these supported catalysts can customarily lead to higher space-time conversions than lower contents. In general, the supported catalysts used will contain from 0.1 to 90% by weight, preferably from 0.5 to 40% by weight, based on the total catalyst, of catalytically active metal. Since these active content figures are based on the total catalyst including support material, but the various support materials have very different specific weights and specific surface areas, these figures can at the present time also be undershot or exceeded without adverse repercussions for the result of the process of this invention. It is also possible, of course, for a plurality of the catalytically active metals to be applied to the particular support material. Furthermore, the catalytically active metals can be applied to the support for example by the process of DE-A 2 519 817, EP-A 1 477 219 and EP-A 285 420. In the catalysts of the aforementioned references, the catalytically active metals are present in the form of an alloy which can be produced by thermal treatment and/or reduction of the [lacuna] for example by impregnation with a salt or complex of the aforementioned metals.

The precipitation catalysts and the supported catalysts alike can also be activated in situ at the start of the reaction by the hydrogen present, but preferably these catalysts are activated separately before use.

The hydrogenation effluent obtained in step a) of the process of this invention is subjected to customary methods such as distillation to recover 6-aminocapronitrile with or without hexamethylenediamine (step b)).

In a preferred embodiment, excess ammonia, hydrogen and optionally the hydrogenation catalyst are removed prior to the isolation of 6-aminocapronitrile with or without hexamethylenediamine in step e).

A further preferred embodiment comprises first treating 5-formylvaleronitrile with ammonia at temperatures within the range from 40 to 150° C. (step d') to obtain an ammoniacal effluent. This can take place for example in a prereactor. This reaction can be carried out in the absence or preferably in the presence of an acidic, homogeneous or heterogeneous catalyst. The space velocity of the catalyst (in the case of heterogeneous catalysts) is customarily within the range from 0.1 to 2.0 kg of 5-formylvaleronitrile/l of catalyst • hour.

The ammoniacal effluent can then be freed from the acidic catalyst, if desired (step e').

A further step (step f) comprises reacting the ammoniacal effluent of d'), or the solution of e'), with ammonia and hydrogen in the presence of hydrogenation catalysts selected from the group consisting of copper, rhenium and compounds thereof and also metals and metal compounds of subgroup eight to obtain a hydrogenation effluent, the process generally being carried out in the same way as the process described above.

Thereafter (step g)) 6-aminocapronitrile is recovered in a conventional manner from the hydrogenation effluent with or without hexamethylenediamine.

The acidic catalysts used can be for example zeolites in the H-form, acidic ion exchangers, heteropolyacids, acidic and superacidic metal oxides optionally doped with sulfate or phosphate, and inorganic or organic acids.

Suitable zeolites are for example representatives of the mordenite group or narrow-pored zeolites of the erionite or chabazite type or zeolites of the faujasite type, for example Y-, X- or L-zeolites. This group also includes the "ultrastable" zeolites of the faujasite type, i.e. dealuminized zeolites.

Particularly advantageous zeolites are those having a pentasil structure, such as ZSM-5, ZSM-11 and ZBM-10. They have a five-membered ring composed of $SiO_2$ tetrahedra in common as basic building block. They are characterized by a high $SiO_2/Al_2O_3$ ratio and also by pore sizes between those of the zeolites of type A and those of type X or Y.

The heteropolyacids used according to this invention are inorganic polyacids which, unlike isopolyacids, have at least two different central atoms. Examples are dodecatungstophosphoric acid $H_3PW_{12}O_{40} \cdot xH_2O$, dodecamolybdophosphoric acid $H_3PMo_{12}O_{40} \cdot xH_2O$. In principle, the catalysts and catalyst combinations mentioned in EP-A 158 229 can be used.

Preferred heteropolyacids are heteropolyacids of molybdenum or tungsten with phosphoric acid, telluric acid, selenic acid, arsenic acid, silicic acid, in particular with phosphoric acid.

The protons of the heteropolyacids can be partly replaced by metal ions, in which case alkali and alkaline earth metal ions are preferred.

Preferred acidic ion exchangers are for example crosslinked polystyrenes having sulfonic acid groups.

Examples of acidic metal oxides are $SiO_2$, $Al_2O_3$, $ZrO_2$, $Ga_2O_3$, $PbO_2$, $Sc_2O_3$, $La_2O_3$, $TiO_2$, $SnO_2$ etc. or combinations of individual oxides. The oxides can also be treated with mineral acids, for example sulfuric acid, to raise the acid strength.

Suitable acids are for example mineral acids such as sulfuric acid and phosphoric acid and also organic acids, for example sulfonic acids.

Examples of superacidic metal oxides are sulfate-doped $ZrO_2$ or molybdenum- or tungsten-containing $ZrO_2$.

In a further preferred embodiment, the hydrogenation is carried out over a hydrogenation metal applied to one of the oxidic supports mentioned. After excess hydrogen has been removed with or without the catalyst, the hydrogenation effluent is preferably worked up for 6-aminocapronitrile with or without hexamethylenediamine by fractional distillation.

The process of this invention gives 6-aminocapronitrile with very good conversions, good yields and selectivities. It is also possible, by varying temperature and catalyst space velocity, to obtain mixtures of 6-aminocapronitrile and hexamethylenediamine. In this connection, high temperatures and low catalyst space velocities favor the formation of hexamethylenediamine, while low temperatures and high catalyst space velocities favor the formation of 6-aminocapronitrile.

6-Aminocapronitrile and hexamethylenediamine are important fiber intermediates. 6-Aminocapronitrile can be cyclized to form caprolactam, the monomer for the production of nylon 6.

Hexamethyleneidamine is chiefly reacted with adipic acid to form 6,6 salt, the nylon-6,6 precursor.

EXAMPLES

Example 1

In a 1 l stirred lift autoclave, 100 g of 3-pentenenitrile, 350 g of m-xylene as solvent and 0.08% by weight of cobalt in the form of dicobalt octacarbonyl as catalyst were heated to 105° C. On attainment of the final temperature, the reaction mixture was admixed with a mixture of 50% by volume of CO and 50% by volume of $H_2$ under a pressure of 140 bar. During the reaction, the pressure in the reactor was kept constant by further injection of a gas mixture of 50% by volume of CO and 50% by volume of $H_2$. After a reaction time of 3 hours, the reaction was discontinued by cooling and decompression. A GC analysis of the reaction mixture revealed the following reaction mixture composition (in mol %):

| Conversion | 7.5 (conversion of 3-pentenenitrile) |
|---|---|
| Selectivity | |
| valeronitrile | 9.0 |
| 5-formylvaleronitrile | 39.0 |
| 3- and 4-formylvaleronitrile | 52.0 |

The yield of formylvaleronitriles (sum of 3-, 4- and 5-FVN) was 6.8%, and the molar ratio of 5-formylvaleronitrile to 3- and 4-formylvaleronitrile was 43:57.

Example 2

In a 1 l stirred lift autoclave, 100 g of 3-pentenenitrile, 350 g of m-xylene as solvent and 0.04% by weight of cobalt in the form of dicobalt octacarbonyl as catalyst were heated to 170° C. On attainment of the final temperature, the reaction mixture was admixed with a mixture of 50% by volume of CO and 50% by volume of $H_2$ under a pressure of 280 bar. During the reaction, the pressure in the reactor was kept constant by further injection of a gas mixture of 50% by volume of CO and 50% by volume of $H_2$. After a reaction time of 2 hours, the reaction was discontinued by cooling and decompression. A GC analysis of the reaction mixture revealed the following reaction mixture composition (in mol %):

| Conversion | >99.9 |
|---|---|
| Selectivity | |
| valeronitrile | 41.0 |
| 5-formylvaleronitrile | 16.0 |
| 3- and 4-formylvaleronitrile | 6.4 |
| 6-hydroxycapronitrile | 23.0 |
| 4- and 5-hydroxymethylvaleronitrile | 3.6 |

The yield of 5-formylvaleronitrile and 6-hydroxycapronitrile together was 39% and the molar ratio of 5-formylvaleronitrile to 3- and 4-formylvaleronitrile was 60:40.

Example 3

In a 300 ml HC autoclave with magnetic stirring, 20 g of 3-pentenenitrile, 100 g of toluene as solvent, 100 ppm of rhodium in the form of the complex $Rh(CO)_2acac$ (acac= acetylacetonate, 25 mg) and the bisphosphite of the formula III (557 mg) (six-fold molar excess based on rhodium)

III

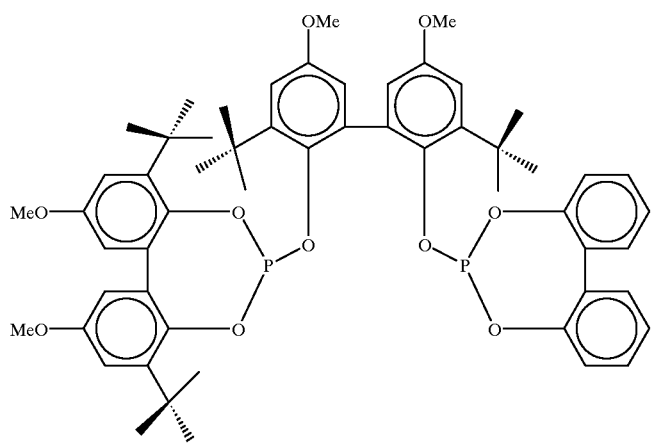

were heated up to 100° C. On attainment of the final temperature the reaction mixture was admixed with a mixture of 50% by volume of CO and 50% by volume of $H_2$ at a pressure of 5 bar. During the reaction, the pressure in the reactor was kept at a constant 5 bar, via a pressure regulator, by further injection of a gas mixture of 50% by volume of CO and 50% by volume of $H_2$. After a reaction time of 5 hours, the reaction was discontinued by cooling down to room temperature and decompression. A GC analysis of the reaction mixture produced the following results (data in mol %):

| Conversion: | >99.9 |
|---|---|
| Selectivity | |
| 2-, 4-pentenenitrile | 19.5 |
| valeronitrile | 21.3 |
| 5-formylvaleronitrile | 29.7 |
| 3- and 4-formylvaleronitrile | 29.5 |

The yield of the product of value, 5-formylvaleronitrile, was 29.7%, and the molar ratio of 5-formylvaleronitrile to 3- and 4-formylvaleronitrile was 50.2:49.8.

Example 4

In a 300 ml HC autoclave with magnetic stirring, 20 g of 3-pentenenitrile, 100 g of Palatinol®C (di-n-butyl phthalate) as solvent, 100 ppm of rhodium in the form of the complex $Rh(CO)_2acac$ (acac=acetylacetonate, 25 mg) and triphenyl phosphite in a 25-fold (based on rhodium) molar excess were heated up to 100° C. On attainment of the final temperature the reaction mixture was admixed with a mixture of 50% by volume of CO and 50% by volume of $H_2$ at a pressure of 5 bar. During the reaction, the pressure in the reactor was kept at a constant 5 bar, via a pressure regulator, by further injection of a gas mixture of 50% by volume of CO and 50% by volume of $H_2$. After a reaction time of 5 hours, the reaction was discontinued by cooling down to room temperature and decompression. A GC analysis of the reaction mixture produced the following results (data in mol %):

| Conversion: | 98.6 |
|---|---|
| Selectivity | |
| 2-, 4-pentenenitrile | 0 |
| valeronitrile | 10.3 |
| 5-formylvaleronitrile | 18.2 |
| 3- and 4-formylvaleronitrile | 71.5 |

The yield of the product of value, 5-formylvaleronitrile, was 17.9%, and the molar ratio of 5-formylvaleronitrile to 3- and 4-formylvaleronitrile was 20:80.

Example 5

In a 300 ml HC autoclave with magnetic stirring, 20 g of 4-pentenenitrile, 100 g of toluene as solvent, 100 ppm of rhodium in the form of the complex $Rh(CO)_2acac$ (acac=acetylacetonate, 25 mg) and the bisphosphite of the formula III (557 mg) (six-fold molar excess based on rhodium) were heated up to 100° C. On attainment of the final temperature the reaction mixture was admixed with a mixture of 50% by volume of Co and 50% by volume of $H_2$ at a pressure of 5 bar. During the reaction, the pressure in the reactor was kept at a constant 5 bar, via a pressure regulator, by further injection of a gas mixture of 50% by volume of CO and 50% by volume of $H_2$. After a reaction time of 5 hours, the reaction was discontinued by cooling down to room temperature and decompression. A GC analysis of the reaction mixture produced the following results (data in mol %):

| Conversion: | >99.9 |
|---|---|
| Selectivity | |
| 2-, 4-pentenenitrile | 34.0 |
| valeronitrile | 6.0 |
| 5-formylvaleronitrile | 49.2 |
| 3- and 4-formylvaleronitrile | 10.8 |

The yield of the product of value, 5-formylvaleronitrile, was 49.2%, and the molar ratio of 5-formylvaleronitrile to 3- and 4-formylvaleronitrile was 82:18.

Example 6

A plurality of hydroformylation effluents obtained according to Example 3 were combined. Distillative removal of 2-, 4-pentenenitrile and valeronitrile left 130 g of a reaction mixture which, according to gas-chromatographic analysis, comprised 48% by weight of 5-formylvaleronitrile and 46% by weight of 4- and 3-formylvaleronitrile. Fractional distillation in a spinning-band column recovered 59 g of 5-formylvaleronitrile of boiling point 93–95° C./3 mbar (purity 99%) and 56 g of 4- +3-formylvaleronitrile of boiling point 77–81° C./3 mbar (purity of 4- +3-isomer 96%).

Example 7

A 300 ml autoclave with sampling port (HC 4 as material of construction) was charged with 11 g of 5-formylvaleronitrile and 3 g of Ru (3%)/Al$_2$O$_3$ (4 mm extrudates) under a protective gas (argon). The autoclave was then sealed, and 150 ml of NH$_3$ were injected. The contents were mixed with a magnetic stirrer. After heating to 80° C. (autogenous pressure: about 39 bar), the mixture was kept at 80° C. for a further 2 hours, and then the total pressure was raised with hydrogen to 70 bar. The pressure of 70 bar was maintained by continued injection of hydrogen. After 25 hours, the autoclave was decompressioned and the hydrogenation effluent was analyzed by gas chromatography. The products formed were 73% of 6-aminocapronitrile and 12% of hexamethylenediamine. The conversion was 100%.

We claim:

1. A process for preparing 6-aminocapronitrile or 6-aminocapronitrile/hexamethylenediamine mixtures, which comprises a) reacting at least one pentenenitrile selected from the group consisting of 2-pentenenitrile, 3-pentenenitrile and 4-pentenenitrile with carbon monoxide and hydrogen in the presence of a catalyst containing at least one element of subgroup eight of the Periodic Table of the Elements as active component to obtain a hydroformylation effluent I, b) optionally removing carbon monoxide, hydrogen and the catalyst from the hydroformylation effluent I to obtain a hydroformylation effluent II, c) removing 5-formylvaleronitrile from said hydroformylation effluent I or II, d) reacting the removed 5-formylvaleronitrile with ammonia and hydrogen in the presence of a hydrogenation catalyst selected from the group consisting of metals or metal compounds of rhenium, copper and the elements of subgroup eight of the Periodic Table of the Elements to obtain a hydrogenation effluent, and e) isolating 6-aminocapronitrile with or without hexamethylenediamine from the hydrogenation effluent, with the proviso that the hydrogenation catalyst of step d) does not contain copper, nickel or copper and nickel as sole components.

2. A process as claimed in claim 1, wherein excess ammonia, hydrogen and optionally the hydrogenation catalyst are removed prior to the isolation of 6-aminocapronitrile with or without hexamethylenediamine in step e).

3. A process as claimed in claim 1, wherein step a) utilizes a catalyst containing cobalt or rhodium or platinum as active component.

4. A process as claimed in claim 1, wherein the reaction of step a) is carried out in the presence of a rhodium carbonyl complex catalyst by adding a cocatalyst selected from the group consisting of triarylphosphines, bis(diarylphosphino) alkanes, triaryl phosphites and polyphosphites of the formulae I and II

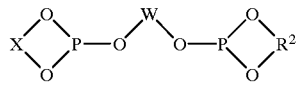

where

X is a bivalent bisarylene radical or R$^1$,

W is a bivalent substituted or unsubstituted arylene, bisarylene or alkylene radical, and R$^1$ and R$^2$ are identical or different and each is a substituted or unsubstituted alkylene or ortho-arylene radical,

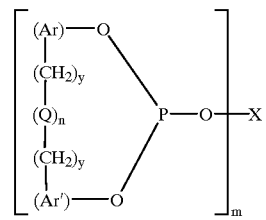

where

Ar and Ar' are identical or different, substituted or unsubstituted arylene radicals having from 6 to 18 carbon atoms;

X is an m-binding radical having from 2 to 30 carbon atoms and selected from the group consisting of alkylene, alkylene-oxy-alkylene, arylene and a radical of the formula

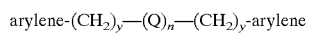

arylene-(CH$_2$)$_y$—(Q)$_n$—(CH$_2$)$_y$-arylene where the arylene radicals are each as defined above and y is 0 or 1;

Q is a bivalent bridging group selected from the group consisting of oxygen, sulfur, —CO—, —CR$^3$R$^4$—, where R$^3$ and R$^4$ are each hydrogen, alkyl having from 1 to 12 carbon atoms or a phenyl, tolyl or anisyl radical, and —NR$^5$—, where R$^5$ is hydrogen or methyl;

n is 0 or 1, and m is an integer from 2 to 6, and optionally containing sulfonate or carboxylate groups.

5. A process as claimed in claim 4, wherein the cocatalyst is added in a molar ratio of cocatalyst (calculated as equivalents of phosphorus) to rhodium within the range from 1:1 to 300:1.

6. A process as claimed in claim 1, wherein the reaction of step a) or d) is carried out in the presence of a solvent.

7. A process as claimed in claim 1, wherein steps d) and e) are replaced by the steps of:

d') treating 5-formylvaleronitrile first with ammonia, optionally in the presence of an acidic catalyst, to obtain an ammoniacal effluent, e') then optionally removing the acidic catalyst to obtain an ammoniacal solution, f) reacting the ammoniacal effluent of d'), or the solution of e'), with ammonia and hydrogen in the presence of a hydrogenation catalyst selected from the group consisting of metals or metal compounds of copper, rhenium and the elements of subgroup eight of the Periodic Table of the Elements to obtain a hydrogenation effluent, and g) isolating 6-aminocapronitrile with or without hexamethylenediamine from the hydrogenation effluent, with the proviso that the hydrogenation catalyst of step f) does not contain copper, nickel or copper and nickel as sole components.

* * * * *